US011103465B2

(12) United States Patent
Robbins et al.

(10) Patent No.: US 11,103,465 B2
(45) Date of Patent: Aug. 31, 2021

(54) TRANS-RESVERATROL TOPICAL MEDICATION FOR THE TREATMENT OF PAIN AND METHOD OF MANUFACTURE THEREOF

(71) Applicant: TED'S BRAIN SCIENCE, INC., Dallas, TX (US)

(72) Inventors: Dennis I. Robbins, Dallas, TX (US); David H. Hitt, Jr., Dallas, TX (US); David H. Hitt, III, Dallas, TX (US)

(73) Assignee: Ted's Brain Science, Inc., Dallas, TX (US)

( * ) Notice: Subject to any disclaimer, the term of this patent is extended or adjusted under 35 U.S.C. 154(b) by 89 days.

(21) Appl. No.: 16/112,844

(22) Filed: Aug. 27, 2018

(65) Prior Publication Data

US 2019/0151254 A1 May 23, 2019

Related U.S. Application Data

(63) Continuation of application No. 15/821,174, filed on Nov. 22, 2017, now abandoned.

(51) Int. Cl.

| | | |
|---|---|---|
| *A61K 31/05* | (2006.01) | |
| *A61K 31/245* | (2006.01) | |
| *A61K 47/10* | (2017.01) | |
| *A61K 47/06* | (2006.01) | |
| *A61K 33/38* | (2006.01) | |
| *A61K 31/125* | (2006.01) | |
| *A61P 31/00* | (2006.01) | |
| *A61K 47/12* | (2006.01) | |
| *A61K 31/606* | (2006.01) | |
| *A61K 31/196* | (2006.01) | |
| *A61K 31/45* | (2006.01) | |
| *A61K 31/167* | (2006.01) | |
| *A61K 47/02* | (2006.01) | |
| *A61K 31/47* | (2006.01) | |
| *A61K 9/10* | (2006.01) | |
| *A61P 25/00* | (2006.01) | |
| *A61K 31/573* | (2006.01) | |
| *A61K 31/18* | (2006.01) | |
| *A61K 31/7036* | (2006.01) | |
| *A61K 31/192* | (2006.01) | |
| *A61K 31/165* | (2006.01) | |
| *A61P 29/00* | (2006.01) | |
| *A61K 31/045* | (2006.01) | |
| *A61K 9/00* | (2006.01) | |

(Continued)

(52) U.S. Cl.
CPC ............ *A61K 31/05* (2013.01); *A61K 9/0014* (2013.01); *A61K 31/045* (2013.01); *A61K 31/125* (2013.01); *A61K 31/165* (2013.01); *A61K 31/167* (2013.01); *A61K 31/18* (2013.01); *A61K 31/192* (2013.01); *A61K 31/196* (2013.01); *A61K 31/245* (2013.01); *A61K 31/47* (2013.01); *A61K 31/573* (2013.01); *A61K 31/60* (2013.01); *A61K 31/606* (2013.01); *A61K 31/7036* (2013.01); *A61K 33/38* (2013.01); *A61K 47/02* (2013.01); *A61K 47/06* (2013.01); *A61K 47/10* (2013.01); *A61K 47/12* (2013.01); *A61K 47/20* (2013.01); *A61P 25/00* (2018.01); *A61P 29/00* (2018.01); *A61P 31/00* (2018.01)

(58) Field of Classification Search
CPC .... A61K 31/05; A61K 9/0014; A61K 31/045; A61K 31/125; A61K 31/165; A61K 31/167; A61K 31/18; A61K 31/192; A61K 31/196; A61K 31/245; A61K 31/47; A61K 31/573; A61K 31/60; A61K 31/606; A61K 31/7036; A61K 33/38; A61K 47/02; A61K 47/06; A61K 47/10; A61K 47/12; A61K 47/20; A61P 31/00; A61P 25/00; A61P 29/00
See application file for complete search history.

(56) References Cited

U.S. PATENT DOCUMENTS

| 4,456,012 A | 6/1984 | Lattin |
|---|---|---|
| 5,069,908 A | 12/1991 | Henley |

(Continued)

FOREIGN PATENT DOCUMENTS

| AU | 1443301 A | 6/2001 |
|---|---|---|
| AU | 2005257883 A1 | 1/2006 |

(Continued)

OTHER PUBLICATIONS

English Translation of WO 2014/116022A1, published 2014, accessed from Google Patents web page Jun. 23, 2018 (Year: 2014).*

(Continued)

*Primary Examiner* — Kortney L. Klinkel
*Assistant Examiner* — William Y Lee
(74) *Attorney, Agent, or Firm* — Saul Ewing Arnstein & Lehr LLP; Domingos J. Silva; Dennis Ostrovsky

(57) ABSTRACT

The invention provides a topical pain medication and a method of manufacturing and suing the same. In one embodiment, the medication includes: (1) enriched resveratrol having a concentration of trans-resveratrol therein that substantially exceeds the natural concentrations of trans-resveratrol in naturally occurring resveratrol, and (2) at least one inactive ingredient configured to mix with the resveratrol to form the topical medication. In one embodiment, the method includes: (1) processing resveratrol to increase the concentration of trans-resveratrol therein and (2) mixing at least one inactive ingredient with the resveratrol to form the topical medication.

10 Claims, 3 Drawing Sheets

(51) Int. Cl.
*A61K 47/20* (2006.01)
*A61K 31/60* (2006.01)

(56) References Cited

U.S. PATENT DOCUMENTS

| | | | |
|---|---|---|---|
| 6,184,248 B1 | 2/2001 | Lee et al. | |
| 6,270,780 B1 * | 8/2001 | Carson | A61K 8/347 424/401 |
| 6,414,037 B1 * | 7/2002 | Pezzuto | A61K 8/347 514/733 |
| 6,469,055 B2 | 10/2002 | Lee et al. | |
| 6,656,925 B2 | 12/2003 | Petrus | |
| 6,738,662 B1 | 5/2004 | Frank | |
| 9,233,085 B1 | 1/2016 | Price et al. | |
| 9,421,189 B2 | 8/2016 | Ianiro et al. | |
| 9,782,448 B2 | 10/2017 | Collins et al. | |
| 2002/0052407 A1 | 5/2002 | Lee et al. | |
| 2002/0119952 A1 | 8/2002 | Petrus | |
| 2004/0037903 A1 | 2/2004 | Lemmo et al. | |
| 2006/0251750 A1 | 11/2006 | Tabor | |
| 2008/0070991 A1 | 3/2008 | Cella et al. | |
| 2010/0076035 A1 | 3/2010 | Carter et al. | |
| 2011/0251242 A1 * | 10/2011 | Bonda | A61K 8/361 514/337 |
| 2013/0252924 A1 | 9/2013 | Penninger et al. | |
| 2014/0134261 A1 | 5/2014 | Singh et al. | |
| 2014/0186306 A1 | 7/2014 | Plante et al. | |
| 2014/0199391 A1 | 7/2014 | Birbara | |
| 2014/0213537 A1 | 7/2014 | Robert et al. | |
| 2014/0349969 A1 | 11/2014 | Penninger et al. | |
| 2016/0143861 A1 | 5/2016 | Hom | |
| 2016/0375078 A1 | 12/2016 | Wurts | |
| 2017/0296488 A1 | 10/2017 | Robert et al. | |

FOREIGN PATENT DOCUMENTS

| | | |
|---|---|---|
| AU | 2005203059 A1 | 2/2006 |
| AU | 2006200823 A1 | 3/2006 |
| AU | 2009212783 A1 | 9/2009 |
| AU | 2009274584 A1 | 1/2010 |
| AU | 2011328009 A1 | 5/2013 |
| AU | 2013257951 A1 | 1/2015 |
| AU | 2014227807 A1 | 11/2015 |
| AU | 2014233388 A1 | 11/2015 |
| AU | 2014233420 A1 | 11/2015 |
| AU | 2015305373 A1 | 3/2017 |
| AU | 2015371308 A1 | 8/2017 |
| AU | 2016229413 A1 | 10/2017 |
| AU | 2016248988 A1 | 10/2017 |
| CA | 2339049 A1 | 3/2000 |
| CA | 2390655 A1 | 5/2001 |
| CA | 2312505 A1 | 12/2001 |
| CA | 2412435 A1 | 12/2001 |
| CA | 2460326 A1 | 3/2003 |
| CA | 2443313 A1 | 3/2004 |
| CA | 2512330 A1 | 1/2006 |
| CA | 2567848 A1 | 1/2006 |
| CA | 2336682 C | 10/2006 |
| CA | 2676609 A1 | 7/2008 |
| CA | 2731242 A1 | 1/2010 |
| CA | 2817290 A1 | 5/2012 |
| CA | 2358958 C | 7/2012 |
| CA | 2893342 A1 | 6/2014 |
| CA | 2906765 A1 | 9/2014 |
| CA | 2906838 A1 | 9/2014 |
| CA | 2906873 A1 | 9/2014 |
| CA | 2909633 A1 | 9/2014 |
| CA | 2958580 A1 | 2/2016 |
| CA | 2970917 A1 | 6/2016 |
| CA | 2972065 A1 | 6/2016 |
| CA | 2978301 A1 | 9/2016 |
| CA | 2958794 A1 | 1/2017 |
| CN | 1964627 A | 5/2007 |
| CN | 101516364 A | 8/2009 |
| EP | 1109553 A1 | 6/2001 |
| EP | 1242063 A1 | 9/2002 |
| EP | 1289369 A1 | 3/2003 |
| EP | 1755391 A2 | 2/2007 |
| EP | 2007366 A2 | 12/2008 |
| EP | 2040696 A2 | 4/2009 |
| EP | 2674161 A1 | 12/2013 |
| EP | 2311454 B1 | 3/2015 |
| JP | 5339373 B2 | 8/2013 |
| KR | 20090028836 A | 3/2009 |
| KR | 101435228 B1 | 8/2014 |
| WO | 0013685 A1 | 3/2000 |
| WO | 0134138 A1 | 5/2001 |
| WO | 0195727 A1 | 12/2001 |
| WO | 2006001982 A2 | 1/2006 |
| WO | 2007112366 A2 | 10/2007 |
| WO | 2008006581 A2 | 1/2008 |
| WO | 2009129627 A1 | 10/2009 |
| WO | 2012012887 A1 | 2/2012 |
| WO | 2014052640 A1 | 4/2014 |
| WO | WO-2014116022 A1 * | 7/2014 ............ A61Q 19/02 |
| WO | 2015006651 A1 | 1/2015 |
| WO | 2017147719 A1 | 9/2017 |

OTHER PUBLICATIONS

Amri, et al., "Administration of Resveratrol: What Formulation Solutions to Bioavailability Limitations?," J Controlled Rel, vol. 158, No. 2, 2012, pp. 182-193.

Johnson, et al., "Transcutaneous electrical nerve stimulation for the management of painful conditions: focus on neuropathic pain," Expert Review of Neurotherapeutics, vol. 11, No. 5, 2011, pp. 735-753.

Tseng, et al., "Production of Silver Ions from Colloidal Silver by Nanoparticle Iontophoresis System," J Nanosci Nanotech, vol. 11, No. 3, 2011, pp. 1991-1995.

Williams, et al., "Penetration enhancers," Advanced Drug Delivery Reviews, 64, 2012, pp. 128-137.

* cited by examiner

TRANS-RESVERATROL TOPICAL MEDICATION FOR THE TREATMENT OF PAIN AND METHOD OF MANUFACTURE THEREOF

CROSS-REFERENCE TO RELATED APPLICATIONS

This application is a continuation of, and claims priority to, U.S. patent application Ser. No. 15/821,174, filed Nov. 22, 2017, which is hereby incorporated herein by reference in its entirety.

TECHNICAL FIELD

This application is directed, in general, to the pharmacological treatment of pain, itching, and/or inflammation associated with certain medical conditions, by use of a topical pharmaceutical composition and/or a wound dressing, comprising specific agents for the mitigation of pain and/or infection.

BACKGROUND

Pain describes a sensation affecting one or more parts of a human or animal body, resulting in distress and a desire to eliminate or mitigate the sensation and/or its source. According to the definition provided by the International Association for the Study of Pain, "[p]ain is an unpleasant sensory and emotional experience associated with actual or potential tissue damage, or described in terms of such damage" (see, International Association for the Study of Pain: Pain Definitions," Retrieved 12 Jan. 2015, derived from Bonica, "The need of a taxonomy," Pain; 6(3):247-8. doi:10.1016/0304-3959(79)90046-0. PMID 460931) (1979).

5' adenosine monophosphate-activated protein kinase, or "AMPK," is an enzyme that plays a role in cellular energy homeostasis (see, e.g., en dot wikipedia dot org/wiki/AMP-activated_protein_kinase). AMPK is expressed in various types of tissue, including the liver, brain, and skeletal muscle. AMPK activation results in the stimulation of hepatic fatty acid oxidation and ketogenesis, inhibition of cholesterol synthesis, lipogenesis, and triglyceride synthesis, inhibition of adipocyte lipolysis and lipogenesis, stimulation of skeletal muscle fatty acid oxidation and muscle glucose uptake, and modulation of insulin secretion by pancreatic beta-cells (supra, and, Winder, et al., "AMP-Activated Protein Kinase, a Metabolic Master Switch: Possible Roles in Type 2 Diabetes," Am. J. Physiol. 277 (1 Pt 1): E1-10. PMID 10409121, July 1999). Various research efforts have indicated a promising role for AMPK activation in the mitigation of pain, including neuropathic pain and nociceptive pain (see, Price, et al., "AMPK: An Emerging Target for Modification of Injury-Induced Pain Plasticity," Neurosci. Lett.; 557 Pt A:9-18. doi:10.1016/j.neulet.2013.06.060. Epub 2013 Jul. 3, 2013 Dec. 17, and, Tillu, et al., "Resveratrol Engages AMPK to Attenuate ERK and mTOR Signaling in Sensory Neurons and Inhibits Incision-Induced Acute and Chronic Pain," J. Mol. Pain. 8:5. doi: 10.1186/1744-8069-8-5, 2012 Jan. 23, both incorporated herein by reference). In this research, the administration of AMPK activators, also called agonists, e.g., resveratrol, has shown efficacy in mitigation of pain in an animal model (rodents).

SUMMARY

One aspect provides a topical pain medication (or pharmaceutical composition). In one embodiment, the medication or pharmaceutical composition comprises: (1) enriched resveratrol having a percentage of trans-resveratrol therein that is enriched over the percentage of trans-resveratrol in naturally occurring resveratrol, and (2) at least one inactive ingredient, wherein the pharmaceutical composition or medication is formulated for topical administration.

Another aspect provides a method of manufacturing a topical pain medication (or pharmaceutical composition). In one embodiment, the method includes: (1) processing resveratrol to increase the percentage or concentration of trans-resveratrol therein and (2) mixing at least one inactive ingredient with the enriched resveratrol to form the topical medication (or pharmaceutical composition).

As used herein, "enriched resveratrol" refers to a composition comprising or consisting of resveratrol, which contains a higher percentage or concentration of trans-resveratrol as compared to non-enriched naturally occurring resveratrol.

BRIEF DESCRIPTION

Reference is now made to the following descriptions taken in conjunction with the accompanying drawings, in which.

DETAILED DESCRIPTION

Figure 4:
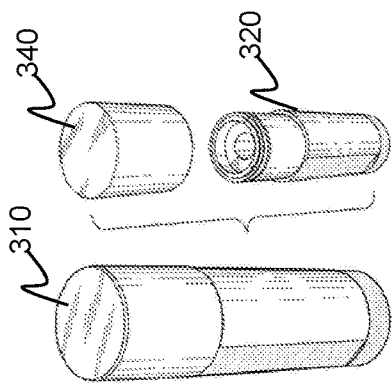
FIG. 4 is an elevational view of another embodiment of a solid stick-type applicator.

Research described above has demonstrated that the administration of AMPK activators, also called agonists, e.g., resveratrol, has shown efficacy in mitigation of pain in an animal model (rodents). The method of administration of AMPK in animal models is injection.

Resveratrol, a polyphenol, occurs naturally in grapes, peanuts, and a number of other plants. It is commonly found in foods and drinks made from grapes and peanuts, and in a number of herbal remedies. As a constituent of red wine, resveratrol has been identified as one possible explanation for the "French paradox," i.e. the finding that the incidence of coronary heart disease is relatively low in southern France despite the high intake of dietary saturated fats or similar risk factor profile (Hendler, et al., "Resveratrol," PDR for Nutritional Supplements, Medical Economics Thomson Healthcare, Montvale, N.J., pp. 397-401). Recent reports on the potential for resveratrol to inhibit the development of cancer and extend life expectancy in animal and cell culture models have continued to generate scientific interest. Available scientific evidence shows that resveratrol has a wide range of desirable biological effects, such as cardioprotection (Hung, et al., "Cardioprotective Effect of Resveratrol, a Natural Antioxidant Derived from Grapes," Cardiovascular Research 47:549-555 (2000)), chemoprevention (Jang, et al., "Cancer Chemopreventive Activity of Resveratrol," Drugs Experimental and Clinical Research 25:65-77 (1999), anticancer (Gusman, et al., "A Reappraisal of the Potential Chemopreventive and Chemotherapeutic Properties of Resveratrol," Carcinogenesis 22:1111-1117 (2003)) and prolongation of life-span in several species (Howitz, et al., "Small Molecule Activators of Sirtuins Extend *Saccharomyces Cerevisiae* Lifespan," Nature 425:191-196 (2003); Valenzano, et al., "Resveratrol Prolongs Lifespan and Retards the Onset of Age-related Markers in a Short-lived Vertebrate," Current Biology 16:296-300 (2006); and Horn, et al., "Oncogenicity Evaluation of Resveratrol in p53(+/−) (p53 Knockout) Mice," Food and Chemical Toxicology 45:55-63 (2007)). The method of administration of resveratrol in the above-cited studies is injection or oral.

It is still further realized herein that a topical medication containing resveratrol is effective to activate AMPK and thereby reduce pain. However, it is recognized that increasing the concentration of resveratrol in a topical preparation past several percent causes the preparation begin to feel grainy and greasy, which are undesirable attributes for a topical preparation and should be avoided.

It is yet further realized herein that resveratrol exists naturally in both cis- and trans-stereoisomeric forms and that both cis- and trans-resveratrol also naturally occur in their respective glucoside forms (bound to a glucose molecule). Resveratrol-3-O-β-glucoside is also called piceid. Trans-resveratrol is chemically known as 3,4',5-stilbenetriol or 3,4',5-trihydroxystilbene. The chemical structure of trans-resveratrol is:

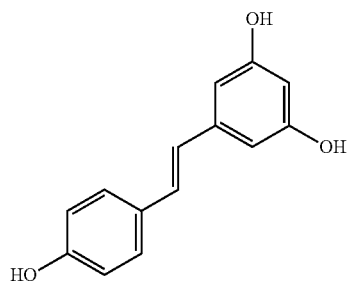 [SMILES: Oc1ccc(/C=C/c2cc(O)cc(O)c2)cc1]

It is still yet further realized herein that trans-resveratrol is the isomer of resveratrol that activates AMPK. Cis-resveratrol appears not to activate AMPK to any meaningful degree or extent. It is thus realized herein that including cis-resveratrol in a topical medication would be particularly disadvantageous, because it would contribute to the grainy or greasy feeling of the medication without contributing to its AMPK-activating efficacy.

Accordingly, introduced herein is a topical pain medication (or pharmaceutical composition) including enriched resveratrol having a percentage or concentration of trans-resveratrol therein that is higher than (in certain embodiments, by more than 5%) the percentage or concentration of trans-resveratrol in naturally occurring resveratrol. In one embodiment, the enriched resveratrol is refined from a resveratrol plant extract to yield an unnaturally high percentage or concentration of trans-resveratrol. In an alternative embodiment, the enriched resveratrol is synthesized and contains an unnaturally high percentage or concentration of trans-resveratrol as compared to the naturally occurring resveratrol. The topical pain medication further includes at least one inactive ingredient mixed with the resveratrol. The at least one inactive ingredient serves to make the medication smoother and creamier or gelatinous and therefore less grainy and less greasy. The at least one inactive ingredient may also partially determine the overall viscosity of the medication, change its texture or scent or increase the rate at which the medication is absorbed through the skin.

In various embodiments, the overall resveratrol concentration (cis- and trans-resveratrol together) is at least 0.8% by volume of the topical pain medication. In other embodiments, the total resveratrol concentration is about 1% by volume of the topical pain medication. In other embodiments, the total resveratrol concentration is about 2% by volume of the topical pain medication.

Another aspect provides a method of manufacturing a topical pain medication. In one embodiment, the method includes: (1) processing resveratrol to increase the percentage or concentration of trans-resveratrol therein and (2) mixing at least one inactive ingredient with the resveratrol to form the topical medication.

As those skilled in the pertinent art understand, resveratrol is naturally found in a wide variety of plants. Natural concentrations of trans-resveratrol generally vary between about 25 and 50% of the overall (cis- and trans-) resveratrol concentration. A trans-resveratrol concentration or percentage that substantially exceeds natural concentrations is defined herein as being a concentration or percentage of trans-resveratrol that exceeds natural concentrations by at least 5%. This concentration or percentage is not found in naturally occurring resveratrol.

For example, if the highest natural concentration of trans-resveratrol is about 50% of the overall (cis- and trans-) resveratrol concentration, a trans-resveratrol concentration that substantially exceeds natural concentrations would be at least a 55% concentration. For example, if the highest natural concentration of trans-resveratrol is about 70% of the overall (cis- and trans-) resveratrol concentration, a trans-resveratrol concentration that substantially exceeds natural concentrations (or an unnatural concentration of trans-resveratrol) would be at least a 75% concentration. In various embodiments described herein, trans-resveratrol concentrations equal or exceed 90%, 95%, 98% and 99% pure trans-resveratrol. In all cases, increasing the trans-resveratrol concentration to above natural concentrations requires the resveratrol to be subjected to at least one man-made process of some kind.

Several methods, including high-performance liquid chromatography (HPLC), gas chromatography (GC), gas chromatography-mass spectrometry (GC-MS), and capillary electrophoresis (CE) have been employed to extract resveratrol from wine and to isolate the trans- and cis-isomers of resveratrol (National Institute of Environmental Health Sciences, "Trans-Resveratrol, [501-36-0], Review of Toxicological Literature under Contract No. NO1-ES-65402, Integrated Laboratory Systems, P.O. Box 13501, Research Triangle Park, N.C., pp. 1-64 (2002)). Resveratrol (>98% purity) can be isolated from the plant, *Polygonum cuspidatum*, by employing high-speed counter-current chromatography (Yang, et al., "Large-scale Separation of Resveratrol, Anthragylcoside A and Anthraglycoside B from *Polygonum Cuspidatum* Sieb. Et Zucc by High-Speed Counter-current Chromatography," Journal of Chromatography A919:443-448 (2001)).

In one embodiment, trans-resveratrol is prepared in the form of off-white to cream-colored powder with >99% purity as determined by high-performance liquid chromatography (HPLC) methodology. The resulting powder has a melting point of 260-264° C. Trans-resveratrol has been shown to be stable over long periods of time (over two years) in well-sealed containers kept away from light.

In a more specific embodiment, resveratrol is extracted from roots of *P. cuspidatum*. Before the extraction process, the plant root is identified and confirmed as *P. cuspidatum* Sieb. Et Zucc (Knotweed herb, bushy knotweed or Japanese knotweed). Trans-resveratrol is isolated by solvent extraction, and the purified product is reported to contain >99% trans-resveratrol. The majority of the resveratrol in the root is in the form of piceid (glucosidic form of resveratrol). The concentration of piceid and resveratrol in *P. cuspidatum* root is generally between 1-2% and 0.1-0.3%, respectively. The root is dried and cut to small pieces. The extraction of resveratrol from the *P. cuspidatum* root also results in extraction of piceid. Piceid is extracted from the pieces of roots with ethanol. The piceid extract is evaporated to dryness under reduced pressure. The isolated piceid is hydrolyzed with sulfuric acid. Hydrolyzation of 1 g piceid yields approximately 0.58 g resveratrol. Normally hydrolysis produces a product containing approximately 50% resveratrol. Subsequent purification steps results in highly purified resveratrol (>99%) concentrate. The solvents and acids used in the isolation and purification process may be cosmetic or food grade.

Alternatively, trans-resveratrol is currently commercially available from many sources, e.g., on the Internet through Alibaba.com. For example, bulk powder 98% pure trans-resveratrol, called "*P. Cuspidatum* Root Extract," is commercially available from Hunan Nutramax, Inc., of Hunan, China. As a further example, "Factory Supply Giant Knotweed Extract, Trans Resveratrol Bulk Powder," is commercially available from Xi'an Arisun ChemPharm Co., Ltd., of Shaanxi, China.

Disclosed herein are various ways to treat pain via topical administration of a therapeutically effective amount of trans-resveratrol. Medication containing trans-resveratrol may be employed to treat pain resulting from conditions such as: shingles (herpes zoster), post-herpetic neuralgia (PHN), gout, migraine (when applied topically to the facial region near the ophthalmic, maxillary and/or mandibular branches), trigeminal neuralgia, CRPS (Complex Regional Pain Syndrome, also known as Reflexive Sympathetic Dystrophy), diabetic neuropathy, peripheral neuropathy, rheumatoid arthritis, insect-related wheals, urushiol-related rash (e.g., poison ivy), psoriasis, herpes simplex, atopic dermatitis (eczema), contact dermatitis, allergic dermatitis, neurotrophic ulcers, first- and second-degree burns (e.g., sunburn and chemical), fibromyalgia, rubeola, and acne.

Various aspects of the disclosure herein include a trans-resveratrol-based topical medication for the treatment of certain specific medical conditions, methods of using the topical medication and/or a wound dressing employing the topical medication. The topical medication may be formulated in the form of a cream or a gel, with the inclusion of various inactive ingredients, including emulsifiers, moisturizers, and other ingredients intended to optimize the ease of topical application of the medication, and address aesthetic issues, including texture, viscosity, and scent. In various aspects, the inactive ingredients can include glycerin, phenoxyethanol, and water. In various aspects, the pharmaceutical compositions includes at least one other inactive ingredient that affects the ease of topical application of the pharmaceutical composition or affects the aesthetic properties of the pharmaceutical composition.

The wound dressing described herein includes a therapeutically effective amount of a topical AMPK agonist, in combination with an antimicrobial agent. A wound dressing is intended for the treatment of various injuries and medical conditions. Synergistic benefit is expected to be achieved by incorporating the AMPK agonist in the dressing; pain resulting from the injury or condition could be mitigated, and by incorporating an antimicrobial agent, infection is expected to be suppressed. The suppression of infection is expected to result in less frequent changes of the wound dressing, and less pain and distress to the patient. Silver has been found to be particularly effective as an antimicrobial agent when incorporated into wound dressings. The silver ion $Ag+$ is bioactive, and in sufficient concentration, it readily kills bacteria (see, e.g., en dot wikipedia dot org/wiki/Medical_uses_of_silver). A wound dressing incorporating silver as an antibacterial agent, in combination with an AMPK agonist for reduction of pain is expected to be particularly effective in promoting healing and reducing distress to the patient.

Various containers or applicators that may be used to dispense or apply the topical pain medication introduced herein to the skin or intra-nasally will now be described.

Figure 1:
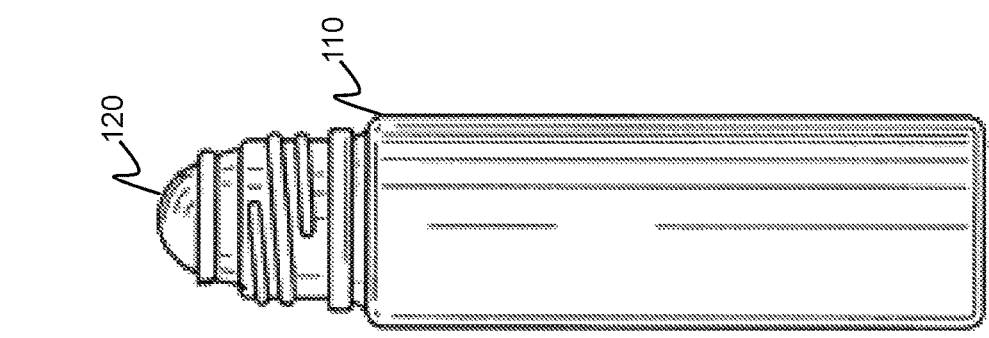
FIG. 1 is an elevational view of one embodiment of a roll-on applicator.

FIG. 1 is an elevational view of one embodiment of a roll-on applicator. The roll-on applicator embodiment has a container 110 configured to contain a quantity of medication (not shown) in liquid form. A roller 120 is captured in a receptacle at a dispensing end of its container, allowing it to rotate in any direction. Liquid medication (which may be a cream or gel) is conveyed on the surface of the roller from within the container to the skin, where it is applied. A cap (not shown) can cover the roller 120 when not in use to inhibit drying.

Figure 2:
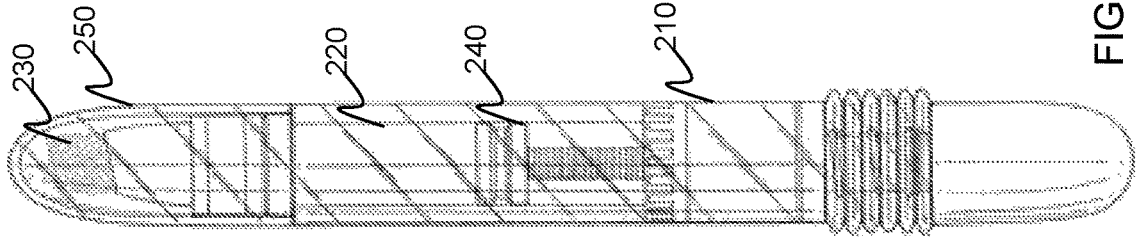
FIG. 2 is an elevational view of one embodiment of a pen-type applicator.

FIG. 2 is an elevational view of one embodiment of a pen-type applicator. The pen-type applicator embodiment has a body 210 configured to contain a quantity of medication (not shown) in liquid form in a reservoir 220 thereof. A wick 230 is in fluid communication with the reservoir 220. The medication is applied by applying pressure to the reservoir 220 using an actuator 240, whereupon the medication is forced into and through the wick 230, at which point it becomes available for application. A cap 250 can cover the wick 230 when not in use to inhibit drying.

Figure 3:
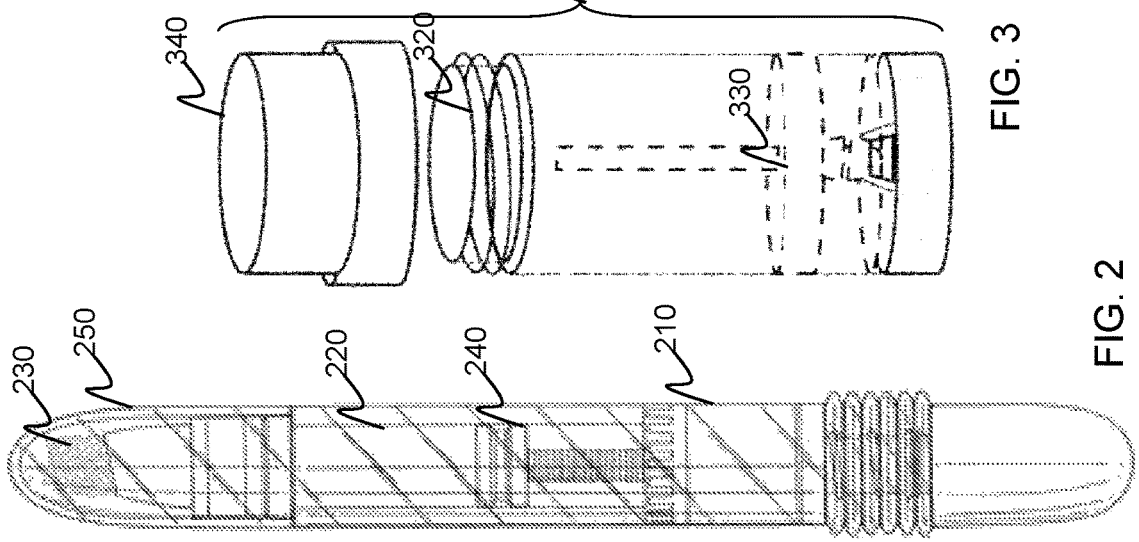
FIG. 3 is an elevational view of one embodiment of a solid stick-type applicator.

FIG. 3 is an elevational view of one embodiment of a solid stick-type applicator 310. The solid stick-type applicator embodiment has a container 320 configured to contain a quantity of medication (not shown) in solid form (often a very thick paste). An actuator 330 may be used to advance the medication until it protrudes from an end of the body 310. The medication may then be applied. A cap 340 can cover the exposed end of the medication to inhibit drying. In the embodiment of FIG. 3, the cap 340 screws onto and off of the container 320. FIG. 4 is an elevational view of another embodiment of a solid stick-type applicator in which the cap 340 is press-fit on the container 320.

Figure 5:
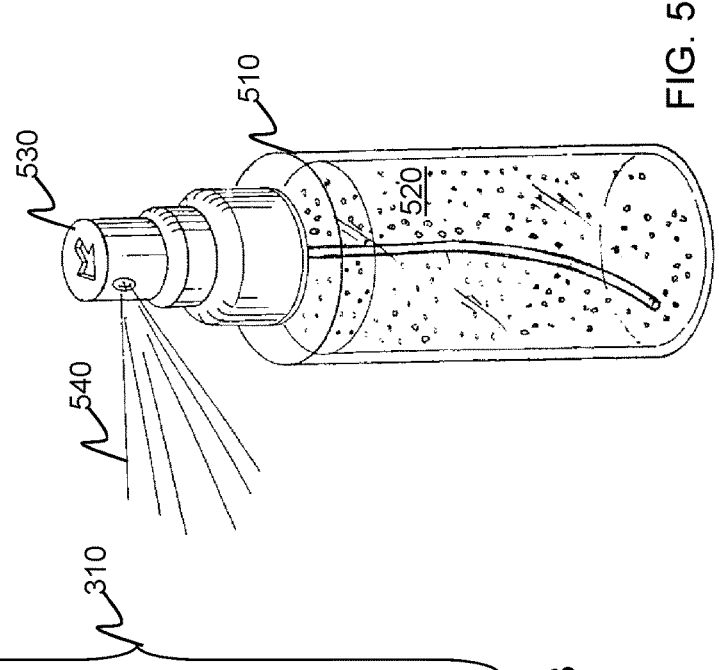
FIG. 5 is an elevational view of one embodiment of a spray bottle.

FIG. 5 is an elevational view of one embodiment of a spray bottle. The spray bottle embodiment has a reservoir 510 configured to contain a quantity of medication 520 in liquid form. A spray head 530 is depressed, perhaps repeatedly, to cause the medication to be drawn up into it, where it is atomized and delivered as a spray 540 for application.

Figure 6:
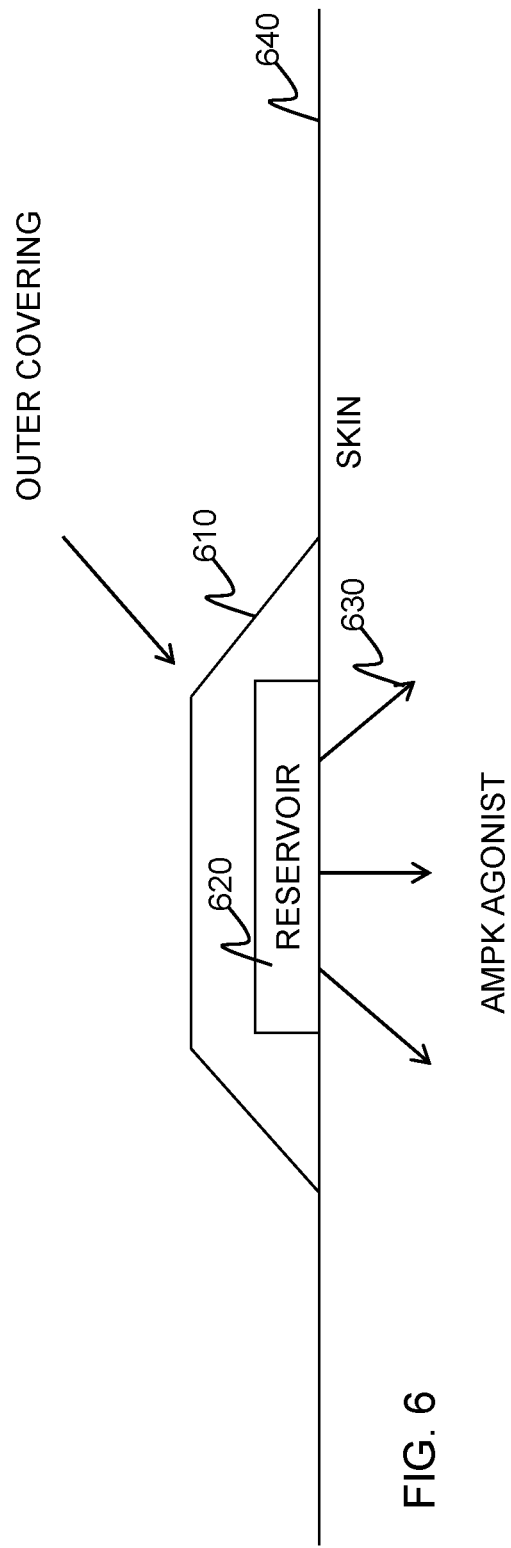
FIG. 6 is an elevational view of one embodiment of a transdermal patch.

In one embodiment, the topical pain medication is delivered by incorporation into a transdermal patch which is applied to the skin of the patient. FIG. 6 is an elevational view of one embodiment of a transdermal patch having an outer covering 610 and a reservoir 620. The patch is applied to skin 630, at which point it begins to deliver topical pain medication 640 transdermally. Such application method is expected to enhance delivery of medication to areas of subcutaneous pain by minimizing loss of medication due to friction with clothing or surroundings. The transdermal patch may further include one or more other medications, which may act synergistically in treating the pain symptoms of a patient.

Figure 7:
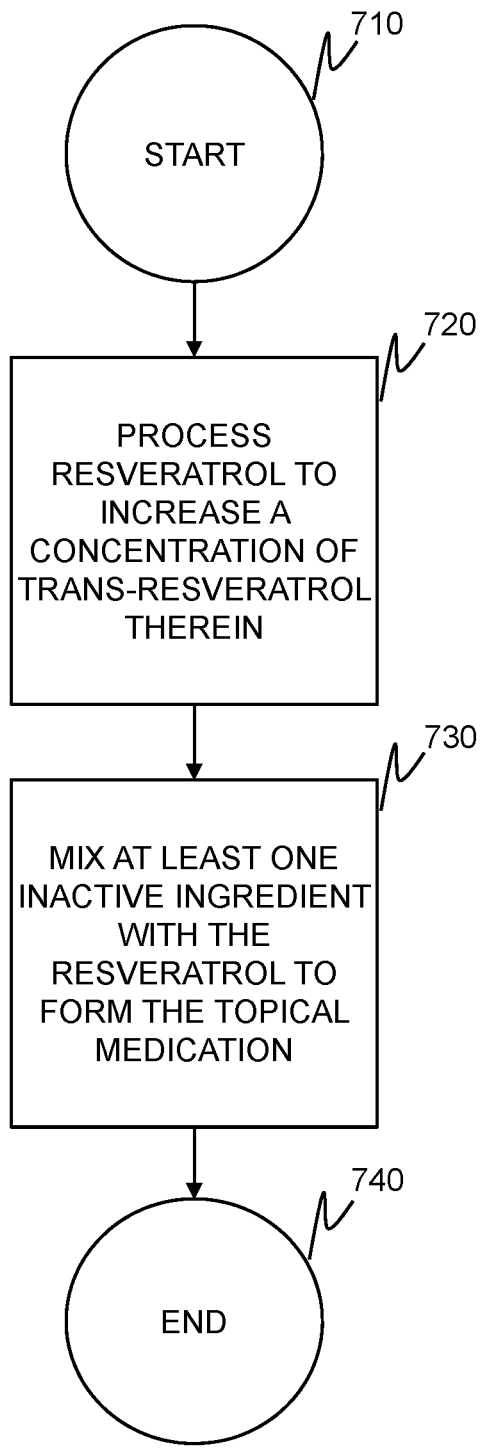
FIG. 7 is a flow diagram of one embodiment of a method of manufacturing a topical pain medication.

FIG. 7 is a flow diagram of one embodiment of an iontophoretic transdermal method. The method begins in a start step 710. In a step 720, resveratrol is processed to increase a concentration of trans-resveratrol therein. In a step 730, at least one inactive ingredient is mixed with the resveratrol to form the topical medication. The medication may then be placed in a container or applicator, or incorporated in a transdermal patch, as described above. The method ends in an end step 740.

Those skilled in the art to which this application relates will appreciate that other and further additions, deletions, substitutions and modifications may be made to the described embodiments.

What is claimed is:

1. A method of treating pain in a subject, the method comprising topically administering to the subject a pharmaceutical composition consisting of:
    inactive ingredients glycerin, phenoxyethanol, and water;
    at least one other inactive ingredient that affects the ease of topical application of the pharmaceutical composition or affects the aesthetic properties of the pharmaceutical composition,
    resveratrol comprising at least 90% trans-resveratrol, and
    an additional agent selected from the group consisting of methyl salicylate, trolamine salicylate, menthol, camphor, lidocaine, benzocaine, dibucaine, prilocaine, capsaicin, diclofenac sodium gel, hydrocortisone, clobetasol, diphenhydramine, ibuprofen, and ketoprofen.

2. The method of claim 1, wherein the resveratrol concentration is at least 0.8% mass by volume of the composition.

3. The method of claim 2, wherein the resveratrol concentration is about 1% mass by volume of the composition.

4. The method of claim 2, wherein the resveratrol concentration is about 2% mass by volume of the composition.

5. The method of claim 1, wherein the pharmaceutical composition is applied using an application device configured to contain the pharmaceutical composition.

6. The method of claim 5, wherein the application device is selected from the group consisting of a roll-on applicator, a pen-type applicator, a solid stick-type applicator, a spray bottle, and a wound dressing.

7. The method of claim 1, wherein the pain is caused by a condition selected from the group consisting of shingles, Post-Herpetic Neuralgia (PHN), gout, a migraine, trigeminal neuralgia, Complex Regional Pain Syndrome (CRPS), diabetic neuropathy, peripheral neuropathy, rheumatoid arthritis, an insect-related wheal, a urushiol-related rash, psoriasis, herpes simplex, atopic dermatitis, contact dermatitis, allergic dermatitis, a neurotrophic ulcer, a burn, fibromyalgia, rubeola, acne, itching, repetitive motion, blunt force trauma, a laceration, an abrasion, frostbite, and a puncture.

8. The method of claim 1, wherein the resveratrol comprises about 1% to 10% cis-resveratrol.

9. A method of treating pain in a subject, the method comprising topically administering to the subject a pharmaceutical composition consisting of:
    inactive ingredients glycerin, phenoxyethanol, and water;
    at least one other inactive ingredient that affects the ease of topical application of the pharmaceutical composition or affects the aesthetic properties of the pharmaceutical composition;
    resveratrol comprising at least 90% trans-resveratrol;
    an antimicrobial agent; and
    an additional agent selected from the group consisting of methyl salicylate, trolamine salicylate, menthol, camphor, lidocaine, benzocaine, dibucaine, prilocaine, capsaicin, diclofenac sodium gel, hydrocortisone, clobetasol, diphenhydramine, ibuprofen, and ketoprofen.

10. The method of claim 9, wherein the antimicrobial agent is selected from the group consisting of silver, gentamicin, and mafenide acetate.

* * * * *